(12) United States Patent
Simon

(10) Patent No.: US 11,319,361 B2
(45) Date of Patent: May 3, 2022

(54) TREATMENT OF INTESTINAL DYSBIOSIS WITH IMMUNOGLOBIN

(71) Applicant: Michael R. Simon, Ann Arbor, MI (US)

(72) Inventor: Michael R. Simon, Ann Arbor, MI (US)

( * ) Notice: Subject to any disclaimer, the term of this patent is extended or adjusted under 35 U.S.C. 154(b) by 266 days.

(21) Appl. No.: 16/678,780

(22) Filed: Nov. 8, 2019

(65) Prior Publication Data

US 2020/0109185 A1 Apr. 9, 2020

Related U.S. Application Data

(63) Continuation-in-part of application No. 15/205,359, filed on Jul. 8, 2016, now Pat. No. 10,912,955, which is a continuation of application No. 15/014,200, filed on Feb. 3, 2016, now Pat. No. 9,409,996, which is a continuation of application No. 14/264,053, filed on Apr. 28, 2014, now Pat. No. 9,273,129, which is a continuation of application No. 13/214,952, filed on Aug. 22, 2011, now Pat. No. 8,709,413, which is a continuation-in-part of application No. 12/138,758, filed on Jun. 13, 2008, now Pat. No. 8,021,645, which is a continuation-in-part of application No. 11/851,606, filed on Sep. 7, 2007, now Pat. No. 7,794,721, which is a continuation-in-part of application No. 11/839,781, filed on Aug. 16, 2007, now Pat. No. 7,597,891, which is a continuation-in-part of application No. 11/610,154, filed on Dec. 13, 2006, now abandoned.

(51) Int. Cl.
| | | |
|---|---|---|
| C07K 16/06 | (2006.01) | |
| A61K 9/48 | (2006.01) | |
| A61K 39/395 | (2006.01) | |
| A61P 1/00 | (2006.01) | |
| A61K 9/50 | (2006.01) | |
| A61P 37/08 | (2006.01) | |

(52) U.S. Cl.
CPC ............ *C07K 16/06* (2013.01); *A61K 9/4891* (2013.01); *A61K 9/5089* (2013.01); *A61K 39/39591* (2013.01); *A61P 1/00* (2018.01); *A61P 37/08* (2018.01); *C07K 2319/30* (2013.01)

(58) Field of Classification Search
None
See application file for complete search history.

(56) References Cited

U.S. PATENT DOCUMENTS

| | | | |
|---|---|---|---|
| 8,709,413 B2 * | 4/2014 | Simon | A61K 39/39583 424/130.1 |
| 9,273,129 B2 * | 3/2016 | Simon | A61K 39/39583 |
| 9,409,996 B2 * | 8/2016 | Simon | C07K 16/44 |

* cited by examiner

*Primary Examiner* — Nora M Rooney
(74) *Attorney, Agent, or Firm* — Blue Filament Law PLLC

(57) ABSTRACT

A process is provided for inhibiting symptoms of intestinal dysbiosis in a subject that includes the oral administration to the subject suffering from intestinal dysbiosis an IgA, IgM, or a combination thereof. When administered in a therapeutic quantity based on the subject characteristics and the type of IgA or IgM, symptoms of intestinal dysbiosis in that subject are inhibited. Even non-secretory forms of IgA or IgM are effective when administered orally.

17 Claims, No Drawings

TREATMENT OF INTESTINAL DYSBIOSIS WITH IMMUNOGLOBIN

CROSS REFERENCE TO RELATED APPLICATIONS

This application is a continuation-in-part of U.S. patent application Ser. No. 15/205,359 filed Jul. 8, 2016, which in turn is a continuation of U.S. patent application Ser. No. 15/014,200 filed Feb. 3, 2016, now U.S. Pat. No. 9,409,996 which in turn is a continuation of U.S. patent application Ser. No. 14/264,053 filed Apr. 28, 2014, now U.S. Pat. No. 9,273,129, which in turn is a continuation of U.S. patent application Ser. No. 13/214,952 filed Aug. 22, 2011, now U.S. Pat. No. 8,709,413, that in turn is a continuation-in-part of U.S. patent application Ser. No. 12/138,758 filed Jun. 13, 2008, now U.S. Pat. No. 8,021,645; which in turn is a continuation-in-part of U.S. patent application Ser. No. 11/851,606 filed Sep. 7, 2007, now U.S. Pat. No. 7,794,721; which in turn is a continuation-in-part of U.S. patent application Ser. No. 11/839,781 filed Aug. 16, 2007, now U.S. Pat. No. 7,597,891; which in turn is a continuation-in-part of U.S. patent application Ser. No. 11/610,154 filed Dec. 13, 2006. The contents of these applications are hereby incorporated by reference.

FIELD OF THE INVENTION

This invention relates in general to processes for the treatment intestinal dysbiosis with orally administered immunoglobulin A (IgA), including secretory IgA, compositions administered in the form of pharmaceutical compositions. Additionally this invention relates in general to processes for the treatment of intestinal dysbiosis with orally administered immunoglobulin M (IgM), including secretory IgM, compositions administered in the form of pharmaceutical compositions.

BACKGROUND OF THE INVENTION

Intestinal dysbiosis is the disturbance of the normal balance of bacterial species in the intestine (Levy M et al 2017). Dysbiosis is a distinct microbial ecological state that is causally linked to the manifestation, diagnosis or treatment of a particular disease (Levy M et al 2017). This often is a consequence of the administration of broad spectrum antibiotics to treat infection (Yoon and Yoon 2018). Intestinal dysbiosis is also found in individuals with a deficiency of IgA in the secretions of the intestinal tract (Fadlallah et al 2018). Intestinal IgA that adheres to intestinal bacteria facilities the symbiotic relationship between the bacteria and the host, such as a person (Nakajima et al 2018, Donaldson et al 2018). Food intolerance includes, but is not limited to, food protein enteropathy and food protein enterocolitis/proctitis (G. Vighi, et al 2008, Caubet et al 2011). Irritable bowel syndrome is sometimes caused by food intolerance (Collins et al 2009). Symptoms of intestinal dysbiosis include upset stomach.
nausea.
constipation.
diarrhea.
bloating.

The symptoms of irritable bowel syndrome can vary significantly from person to person. A partial listing of irritable bowel syndrome symptoms includes:

Abdominal pain
Abdominal distention, bloating, gas, indigestion
Constipation
Diarrhea, chronic or occasional Food allergy is most often attributed to IgE antibodies with antigenic specificity for specific foods (Granato and Piguet 1986; Wang et al 2010). Foods normally induce local intestinal mucosal production of IgA and IgM (Shimoda et al 1999). Food intolerance and allergy are associated with deficiency in IgA (Walker et al 1999, Harrison et al 1976). It has been hypothesized that food antigen IgA may competitively bind to food antigens, and thereby protect the subject from reacting to that food with an allergic response (Possin et al 2010). Food antigen specific IgA is found in the blood plasma (Vojdani 2009, Trajkovski 2008). Food allergy is associated with a relative decrease in food antigen specific IgA in the intestines (Frossard C P at al 2004). Application of antigen-specific IgA to the respiratory mucosa in mice prevents increased airway hyperreactivity in allergic asthma (Schwarze et al 1998; U.S. Pat. No. 5,670,626). Ulcerative colitis is a chronic inflammation of the large intestine. There is decreased mucosal IgA in the intestinal mucosa of patients with ulcerative colitis (Cicalese et al 1995). Food antigen challenge in the presence of Staphylococcal enteroxin B has been shown to induce ulcerative colitis in a mouse disease model (Yang 2005). Non-IgE mediated food intolerance is also known to exist and be most common in infants and young children due to ingested dietary proteins such as those found in cow's milk and soy protein creating profound discomfort. While non-IgE mediated food allergy is rarely life threatening, it can cause significant morbidity in rapidly growing infants and young children. (Jyonouchi, 2008).

The prior art failed to explore orally administered IgAs or IgMs as a potential medicament for the treatment of food allergy and food intolerance.

Thus, there exists a need for an IgA therapeutic or an IgM therapeutic for the treatment of food allergy and food intolerance. There also exists a need to provide such a therapeutic in a dosing form well suited for treating an affected subject.

SUMMARY OF THE INVENTION

A process is provided for inhibiting symptoms of intestinal dysbiosis in a subject that includes the oral administration of an IgA or an IgM. to the subject suffering from food allergy or food intolerance an IgA or an IgM. When administered in a therapeutic quantity based on the subject characteristics and the type of IgA or IgM, symptoms of intestinal dysbiosis in that subject are inhibited. Even non-secretory forms of IgA and IgM are effective when administered orally. The administered immunoglobulin is readily formed from monoclonal or polyclonal sources. Recombinant forms of the immunoglobulins are also operative herein. When the immunoglobulin is IgA, the IgA is readily administered in a dimeric, or polymeric form that optionally includes secretory component. When the immunoglobulin is IgM, the IgM is readily administered in a pentameric form that optionally includes secretory component. Semisynthetic human secretory IgA and semisynthetic human secretory IgM are not natural substances in that they are comprised of a recombinant human secretory component protein in addition to the immunoglobulin.

DETAILED DESCRIPTION OF THE PREFERRED EMBODIMENTS

The present invention has utility as a treatment for intestinal dysbiosis. The process includes treatment with monoclonal- or polyclonal-IgAs that are, dimeric or polymeric and/or secretory IgA; and/or monoclonal- or polyclonal-IgM that are, pentameric and/or secretory IgM. While monomeric IgA is susceptible to gastrointestinal degradation it has been surprisingly found that monomeric immunoglobulin maintains some antibody function after oral administration (Kelly C et al 1997) Because of its resistance to degradation in the gastrointestinal tract, secretory IgA and secretory IgM are generally effective at lower doses. Immunoglobulins have minimal side effects because they are naturally present in the gastrointestinal tract. Dimeric IgA and pentameric IgM according to the present invention may be bound to secretory component in order to mimic natural secretory IgA and natural secretory IgM endogenous to the subject. Alternatively they may be administered without bound secretory component.

As used herein, a "subject" is defined as a human.

As the present invention uses an immunoglobulin rather than a metabolic or immunological inhibitor, an effective treatment is provided which does not disturb the body's metabolism.

The following description of the preferred embodiment(s) is merely exemplary in nature and is in no way intended to limit the invention, its application, or uses.

IgA and IgM in various forms including polyclonal IgA that are monomeric, dimeric or polymeric; and monoclonal- or polyclonal-IgM that is secretory or pentameric are all known to the art, as evidenced for example, by the references incorporated herein.

In one embodiment, the invention provides a process for medical treatment of humans involving the oral administration of secretory IgA which can be derived from a number of sources. One such source for the IgA is pooled human plasma following Cohn cold ethanol fractionation to produce fraction III precipitate as performed by those of skill in the art of protein separation. The IgA byproduct is further purified by adsorption onto jackbean lectin (jacalin) or onto an ion exchange medium in neutral or slightly acidic conditions as performed by those of skill in the art of protein purification. Another source for the IgA is recombinant IgA produced from a hybridoma or a transgenic plant.

A more detailed description of isolation of an IgA component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted byproduct. According to the invention, this unwanted IgA following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the IgA byproduct including the dimeric and polymeric forms during the manufacture of intravenous immunoglobulin. From 4% to 22% of plasma IgA is dimeric and polymeric IgA (Delacroix et al. 1981; Delacroix et al. 1983). The resulting dimeric and polymeric IgA-J chains are purified.

In a preferred embodiment, the compositions of the invention contain, in addition to the IgA component, recombinant secretory component. Human secretory component can be produced by recombinant techniques as described in Crottet et al., Biochem. J. 1999; 341:299-306. The resulting dimeric IgA is further coupled to recombinant secretory component. In a preferred embodiment, the coupling is accomplished by forming disulfide bonds under mildly oxidizing conditions. (Jones 1998) Dimeric IgA containing both J chain and secretory component is again purified by ion-exchange and size exclusion chromatography and/or ultrafiltration as described in Lullau et al., J. Biol. Chem. 1996; 271:16300-16309, Corthesy, Biochem. Soc. Trans. 1997; 25:471-475, and Crottet et al., Biochem. J. 1999; 341:299-306, as performed by those of skill in the art of protein purification. Purified dimeric and polymeric IgA containing secretory component is optionally stabilized for example by the addition of human serum albumin to a final concentration of 5%. The presence of the human J chains and secretory component in the compositions of the invention leads to doses of immunoglobulin A which are more physiologically effective than compositions without such components. These selected additives are natural ligands, detergents, salts, buffers, and chemicals that have been shown to increase the stability of proteins in vivo. It is appreciated that proteins are also readily stabilized through the addition of a stabilizing agent. These agents illustratively include trehalose, glycine betaine, mannitol, L-arginine, L-glutamic acid, potassium citrate, $CuCl_2$, proline, xylitol, $K_2PO_4$, and combinations thereof (Leibly et al., Golovanov et al.).

In still other embodiments, an IgA or IgM is combined with a semi-solid or solid carrier can be further formulated into hard or soft shell gelatin capsules, tablets, or pills. In some embodiments, the hard or soft shell gelatin capsules, tablets, or pills are enterically coated. Exemplary of such enteric coatings are those detailed in U.S. Pat. No. 5,629,001.

In still other inventive embodiments, the IgA or IgM is combined with an antacid. Antacids operative herein illustratively include neutralizing hydroxyl group containing compounds, as well as H2 blockers of sodium bicarbonate, magnesium oxide, magnesium hydroxide, calcium carbonate, magnesium trisilicate, magnesium carbonate, aluminum hydroxide gel, cimetidine, ranitidine or combinations thereof.

Dimeric IgA contains two IgA monomers plus J chain.

The secretory IgA antibodies may be administered alone as a liquid or solid, preferably in a solid powder form and preferably in admixture with a carrier to form a pharmaceutical composition such as a tablet, capsule or suppository.

Since preferred methods of administration are oral with solid oral dosage forms such as tablets and capsules being especially preferred, or enteric installation. These are prepared according to conventional methods known those skilled in the art. The secretory IgA antibodies may also be combined with other pharmaceutically acceptable carriers such as various liquids, proteins or oils which may also provide additional nutritional and/or pharmaceutical benefits. Remington Science and Practice of Pharmacy, 20$^{th}$ ed. (2000).

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged residence in the intestinal lumen of the IgA or IgM can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385,078; 4,518,433; and 4,556,552.

They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Since the effect of the IgA and IgM antibodies is dependent on their reaching the small intestine, preferred tablets or capsules are enteric coated. Alternatively, the active IgA and IgM antibodies can themselves be microencapsulated prior to formulation. Preparation of microcapsules of IgA and IgM antibody as well as preparation of enteric coated tablets or capsules can be achieved by conventional methods as detailed above.

It is appreciated that the therapeutic amount of IgA or IgM depends on the form thereof, with forms subject to gastrointestinal degradation requiring larger doses. Typically amounts of IgA or IgM from about 0.005 mg to 50 grams per day are used and preferably, 1 mg to 40 grams per day. Generally, secretory IgA or IgM are each independently effective as a treatment when provided to the patient at about 10 grams per day. Forms of IgA or IgM that are prone to gastrointestinal degradation are typically effective in doses increased by at least 80% relative to secretory forms. For example, about 5 grams of secretory IgA could be given to a subject per day in a single dose or in divided doses 3 to 4 times per day. Preferably, multiple doses are administered with meals likely containing food allergens. It is appreciated that a physician can readily adjust the doses of the IgA or IgM to be administered based on the subject's response to treatment. Many factors are considered in dose adjustments. Dosages of secretory IgA or secretory IgM for adult humans envisioned by the present invention and considered to be therapeutically effective will range from between about 5 mg to 50 g. However, it is to be understood that doses can readily be adjusted to provide appropriate amounts of the IgA antibody to any subject, including children.

The present invention also provides a process for medical treatment of humans involving the oral administration of monomeric IgA which can be derived from pooled human plasma or monoclonal IgA which can be derived by hybridoma technology (B Cell Design, Limoge, France).

The present invention also provides a process for medical treatment of humans involving the oral administration of secretory IgM which can be derived from pooled human plasma following Cohn cold ethanol fractionation to produce fraction III precipitate as performed by those of skill in the art of protein separation as described above. IgM byproduct is further purified by adsorption onto an ion exchange medium in neutral or slightly acidic conditions as performed by those of skill in the art of protein purification. Another source for the IgM is recombinant IgM produced from a hybridoma.

The invention is further described by reference to the following detailed examples, wherein the processologies are as described below. These examples are not meant to limit the scope of the invention that has been set forth in the foregoing description. Variations within the concepts of the invention are apparent to those skilled in the art.

Example 1

Monoclonal dimeric IgA is obtained from hybridoma technology. The monoclonal IgA is stabilized by the addition of human serum albumin to a final concentration of 5% and encapsulated. The final solution is adjusted to a therapeutic dose of 10 g IgA daily. The IgA is administered to a person suffering with intestinal dysbiosis. One day after initiation of treatment, the intestinal dysbiosis sufferer experiences diminution of his/her symptoms.

Example 2

The process of Example 1 is repeated with the IgA administered with an enteric, encapsulating coating and a lower daily dose of 2 g to achieve a similar result.

Example 3

The process of Examples 2 is repeated with monoclonal IgA replaced with polyclonal IgA that is obtained from pooled human plasma following Cohn cold ethanol fractionation to produce fraction III precipitate. IgA is further purified by adsorption onto an ion exchange medium in neutral or slightly acidic conditions. IgA-J chain dimers and polymers are purified. IgA-J chain dimers and polymers are then further coupled to recombinant secretory component again by disulfide bonding in mildly oxidizing conditions, preferably at a molar ratio of secretory component to IgA-J chain dimers and polymers of 1:1. IgA containing both J chain and secretory component is again purified. Purified IgA containing J chain and secretory component is stabilized by the addition of human serum albumin to a final concentration of 5%. The final solution of secretory IgA is adjusted to a therapeutic dose of 5 mg IgA and is administered to a person suffering with intestinal dysbiosis. One month after initiation of treatment the intestinal dysbiosis sufferer no longer has any symptoms.

Example 4

The process of Example 4 is repeated with monoclonal IgA replaced with polyclonal IgM that is obtained from pooled human plasma following Cohn cold ethanol fractionation to produce fraction III precipitate. IgM is further purified by adsorption onto an ion exchange medium in neutral or slightly acidic conditions. IgM-J chain pentamers are purified. IgM-J chain pentamers are then further coupled to recombinant secretory component again by disulfide bonding in mildly oxidizing conditions, preferably at a molar ratio of secretory component to IgM-J chain pentamers of 1:1. IgA containing both J chain and secretory component is again purified. Purified IgM containing J chain and secretory component is stabilized by the addition of human serum albumin to a final concentration of 5%. The final solution is adjusted to a therapeutic dose of 10 g IgM. The IgM is administered to a person suffering with intestinal dysbiosis. One month after to initiation of treatment the intestinal dysbiosis sufferer no longer has symptoms.

Examples 5-9

Examples 5-9 are repeated with monoclonal IgA replaced with polyclonal IgM per Example 4 to achieve like results.

REFERENCES

Berzofsky J. A., Berkower I. J., Epstein S. L., Monoclonal Antibodies in Chapter 12, Antigen-Antibody Interactions and Monoclonal Antibodies, pp. 455-465 in Fundamental Immunology, Third Edition, W. E. Paul (ed), Raven Press, N Y 1993. Berzofsky et al., Fundamental Immunology, Third Edition, 1993, pp 455-462.

Cicalese L, Duerr R H, Nalesnik M A, Heeckt P F, Lee K K, Schraut W H. Decreased mucosal IgA levelsin ileumof patients with chronic ulcerative colitis. Dig Dis Sci. 1995 April; 40(4): 805-11.

Cohn E. J., Strong L. E., Hughes W. L., Jr., Mulford D. J., Ashworth J. N., Melin M., Taylor H. L., Preparation and Properties of Serum and Plasma Proteins IV. A System for the Separation into Fractions of the Protein and Lipoprotein Components of Biological Tissues and Fluids, J. Am. Chem. Soc. 1946; 68; 459-475.

S. M. Collins, E. Denou, E. F. Verdu, P. Bercik. The putative role of the intestinal microbiota in the irritable bowel syndrome. Digestive and Liver Disease 41 (2009) 850-853

Corthesy B., Recombinant Secretory IgA for Immune Intervention Against Mucosal Pathogens, Biochem. Soc. Trans. 1997, 25; 471-475.

Crottet P., Cottet S., Corthesy B., Expression, Purification and Biochemical Characterization of Recombinant Murine Secretory Component, A Novel Tool in Mucosal Immunology, Biochem. J. 1999, 341; 299-306.

Caubet J C, Nowak-Wegrzyn A. Current understanding of the immune mechanisms of food protein-induced enterocolitis syndrome. Expert Rev Clin Immunol. 2011 May; 7(3):317-27.

Delacroix D. L., Hodgson H. J., McPherson A., Dive C., Vaerman J. P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August; 70(2):230-41

Delacroix D. L., Elkom K. B., Geubel A. P., Hodgson H. F., Dive C., Vaerman J. P. Changes in size, subclass, and metabolic properties of serum immunoglobulin A in liver diseases and in other diseases with high serum immunoglobulin A. J. Clin. Invest. 1983 February; 71(2):358-67.

Donaldson G P, Ladinsky M S, Yu K B, Sanders J G, Yoo B B, Chou W C, Conner M E, Earl A M, Knight R, Bjorkman P J, Mazmanian S K Gut microbiota utilize immunoglobulin A for mucosal colonization. Science. 2018 May 18; 360(6390):795-800. doi: 10.1126/science.aaq0926. Epub 2018 May 3.

Fadlallah J, El Kafsi H, Sterlin D, Juste C, Parizot C, Dorgham K, Autaa G, Gouas D, Almeida M, Lepage P, Pons N, Le Chatelier E, Levenez F, Kennedy S, Galleron N, de Barros J P, Malphettes M, Galicier L, Boutboul D, Mathian A, Miyara M, Oksenhendler E, Amoura Z, Dore J, Fieschi C, Ehrlich S D, Larsen M, Gorochov G. Microbial ecology perturbation in human IgA deficiency. Sci Transl Med. 2018 May 2; 10 (439). pii: eaan1217. doi: 10.1126/scitranslmed.aan1217.

Frossard C P, Hauser C, Eigenmann P A. Antigen-specific secretory IgA antibodies in the gut are decreased in a mouse model of food allergy. J Allergy Clin Immunol. 2004 August; 114(2):377-82.

Granato D A, Piguet P F. A mouse monoclonal IgE antibody anti bovine milk beta-lactoglobulin allows studies of allergy in the gastrointestinal tract. Clin Exp Immunol. 1986 March; 63(3):703-10.

Golovanov A P, Hautberge, G M, Wilson S A, Lian, L-Y. A Simple Method for Improving Protein Solubility and Long-Term Stability. J. Am. Chem. Soc. 2004, 126(29): 8933-8939.

Harrison M, Kilby A, Walker-Smith J A, France N E, Wood C B. Cows' milk protein intolerance: a possible association with gastroenteritis, lactose intolerance, and IgA deficiency. Br Med J. 1976 Jun. 19; 1(6024):1501-4.

Harumi J. Non-IgE Mediated Food Allergy. *Inflammation & Allergy—Drug Targets,* 2008, 7, 000-000.

Jones R. M. L., Schweikart F., Frutiger S., Jaton J-C., Hughes G. J. Thiol-disulfide redox buffers maintain a structure of immunoglobulin A that is essential for optimal in vitro binding to secretory component. Biochimica et Biophysica Acta 1998; 1429:265-274.

Kelly C P, Chetham S, Keates S, Bostwick E F, Roush A M, Castagliuolo I, LaMont J T, Pothoulakis C. Survival of Anti-*Clostridium difficile* Bovine Immunoglobulin Concentrate in the Human Gastrointestinal Tract. Antimicrob Agents Chemother. 1997 February; 41(2):236-41.

Kohler G., Milstein C., Continuous Cultures of Fused Cells Secreting Antibody of Predetermined Specificity, Nature 1975; 256; 495-497.

Leibly D J, Nguyen T N, Kao L T, Hewitt S N, Barrett L K, Van Voorhis, W C. Stabilizing Additives Added during Cell Lysis Aid in the Solubilization of Recombinant Proteins. PLOS ONE. 2012 December; 7 (12): e52482: 1-12.

Levy M, Kolodziejczyk A A, Thaiss C A, Elinav E. Dysbiosis and the immune system. Nat Rev Immunol. 2017 April; 17(4):219-232. doi: 10.1038/nri.2017.7. Epub 2017 Mar. 6.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Nakajima A1, Vogelzang A, Maruya M, Miyajima M, Murata M1, Son A, Kuwahara T, Tsuruyama T, Yamada S, Matsuura M5, Nakase H, Peterson D A, Fagarasan S, Suzuki K IgA regulates the composition and metabolic function of gut microbiota by promoting symbiosis between bacteria. J Exp Med. 2018 Aug. 6; 215(8):2019-2034. doi: 10.1084/jem.20180427. Epub 2018 Jul. 24.

Oncley J. L., Melin M., Richert D. A., Cameron J. W., Gross P. M., Jr., The Separation of the Antibodies, Isoagglutinins, Prothrombin, Plasminogen and β1-Lipoprotein into Subfractions of Human Plasma. J. Am. Chem. Soc. 1949; 71:541-550.

Possin M E, Morgan S, DaSilva D F, Tisler C, Pappas T E, Roberg K A, Anderson E, Evans M D, Gangnon R, Lemanske R F, Gern J E. The relationships among immunoglobulin levels, allergic sensitization, and viral respiratory illnesses in early childhood. Pediatr Allergy Immunol 2010: 21: 990-996.

Schwarze J, Cieslewicz G, Joetham A, L Sun L K, Sun W N, Chang T W, Hamelmann E, W. Gelfand E W. Antigen-specific Immunoglobulin-A Prevents Increased Airway Responsiveness and Lung Eosinophilia after Airway Challenge in Sensitized Mice. Am J Resp Crit Care Med 1998; 158:519-525.

Shimoda M, Inoue Y, Azuma N, Kanno C. Local antibody response in Peyer's patches to the orally administered dietary protein antigen. Biosci Biotechnol Biochem. 1999 December; 63(12):2123-9.

Strong L. E., Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, N Y 1963, pp. 576-602.

Symersky J., Novak J., McPherson D. T., DeLucas L., Mestecky J. Expression of the recombinant human immunoglobulin J chain in *Escherichia coli*. Mol. Immunol. 2000; 37:133-140.

Trajkovski V, Ajdinski L, Spiroski M. Plasma concentration of immunoglobulin classes and subclasses in children with autism in the Republic of Macedonia: retrospective study. Croat Med J. 2004 December; 45(6):746-9.

Vighi G, Marcucci F, Sensi L, G. Di Cara G, Frati F. Allergy and the gastrointestinal system. *Clinical and Experimental Immunology,* 153 (Suppl. 1): 3-6, 2008.

Vojdani A. Detection of IgE, IgG, IgA and IgM antibodies against raw and processed food antigens. Nutr Metab (Lond). 2009 May 12; 6:22

Walker A M, Kemp A S, Hill D J, Shelton M J. Features of transient hypogammaglobulinaemia in infants screened for immunological abnormalities. Arch Dis Child. 1994 March; 70(3): 183-186.

Wang M, Takeda K, Shiraishi Y, Okamoto M, Dakhama A, Joetham A, Gelfand E W. Peanut-induced intestinal allergy is mediated through a mast cell-IgE-FcepsilonRI-IL-13 pathway. J Allergy Clin Immunol. 2010 August; 126(2):306-16, 316.e1-12.

Yang P-C, Wang C-S, An Z-Y. A murine model of ulcerative colitis: induced with sinusitis-derived superantigen and food allergen. BMC Gastroenterology 2005, 5:6.

Yoon M Y, Yoon S S. Disruption of the Gut Ecosystem by Antibiotics. Yonsei Medical Journal (2018), 59 (1): 4

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for inhibiting symptoms of intestinal dysbiosis in a subject comprising:
    administering orally to the subject suffering from intestinal dysbiosis a purified IgA, a purified IgM, or a combination thereof; and
    allowing sufficient time for said IgA or IgM to inhibit symptoms of intestinal dysbiosis in that subject.

2. A process for treating of intestinal dysbiosis in a subject comprising:
    administering orally to the subject suffering from intestinal dysbiosis a purified IgA or a purified IgM or a combination thereof.

3. The process of claim 1 wherein said IgA or IgM is administered and is polyclonal or monoclonal.

4. The process of claim 1 wherein said IgA is dimeric or polymeric.

5. The process of claim 1 wherein said IgM is pentameric.

6. The process of claim 1 wherein said IgA or IgM is recombinant.

7. The process of claim 1 wherein said IgA or IgM is bound to recombinant human secretory component.

8. The process of claim 1 wherein said IgA or IgM is administered as a tablet or a capsule.

9. The process of claim 8 wherein said tablet or said capsule is enterically coated.

10. The process of claim 1, further comprising microencapsulating said IgA or IgM prior to said administration.

11. The process of claim 1 wherein intestinal dysbiosis exacerbates IgA deficiency.

12. The process of claim 1 wherein intestinal dysbiosis causes or exacerbates irritable bowel syndrome.

13. The process of claim 1 wherein said IgA or said IgM is stabilized by the addition of human serum ablumin.

14. The process of claim 1 wherein said IgA or said IgM is stabilized by delivery with an antacid.

15. The process of claim 1 wherein said IgA is derived from an IgA byproduct purified by adsorption onto jackbean lectin.

16. The process of claim 14 wherein said antacid is selected from the group consisting of: neutralizing hydroxyl group containing compounds, sodium bicarbonate, magnesium oxide, magnesium hydroxide, calcium carbonate, magnesium trisilicate, magnesium carbonate, aluminum hydroxide gel, cimetidine, ranitidine or combinations thereof.

17. The process of claim 1 wherein said IgA or said IgM is administered as a liquid.

* * * * *